US00PP27884P3

(12) United States Plant Patent
Kobayashi

(10) Patent No.: US PP27,884 P3
(45) Date of Patent: Apr. 11, 2017

(54) POINSETTIA PLANT NAMED 'PER1912'

(50) Latin Name: ***Euphorbia pulcherrima* Willd.**
Varietal Denomination: PER1912

(71) Applicant: Ruth Kobayashi, Carlsbad, CA (US)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 105 days.

(21) Appl. No.: 14/545,495

(22) Filed: May 12, 2015

(65) Prior Publication Data

US 2016/0338243 P1 Nov. 17, 2016

(51) Int. Cl.
*A01H 5/02* (2006.01)

(52) U.S. Cl.
USPC ..... Plt./306

(58) Field of Classification Search
USPC ..... Plt./263.1, 302, 303, 306
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Poinsettia plant named 'PER1912', characterized by its uniform, upright and mounded plant habit; moderately vigorous growth habit; freely and upright branching habit; dark green-colored leaves; under natural season conditions, plants flower on or about November 25 in Southern California; large inflorescences with salmon pink-colored flower bracts; and good post-production longevity.

1 Drawing Sheet

Botanical designation: *Euphorbia pulcherrima* Willd.
Cultivar denomination: 'PER1912'.

BACKGROUND OF THE INVENTION

The present invention relates to a new and distinct cultivar of Poinsettia plant, botanically known as *Euphorbia pulcherrima* Willd., and hereinafter referred to by the cultivar name 'PER1912'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant is a naturally-occurring whole plant mutation of a proprietary selection of *Euphorbia pulcherrima* Willd. 'PER1270', disclosed in U.S. Plant Pat. No. 24,233. The new Poinsettia plant was discovered and selected by the Inventor from within a population of plants of the mutation parent in a controlled greenhouse environment in Encinitas, Calif. on Sep. 21, 2011.

Asexual reproduction of the new Poinsettia plant by terminal vegetative cuttings in a controlled greenhouse environment in Encinitas, Calif. since January, 2012 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER1912'. These characteristics in combination distinguish 'PER1912' as a new and distinct Poinsettia plant:

1. Uniform, upright and mounded plant habit.
2. Moderately vigorous growth habit.
3. Freely and upright branching habit.
4. Dark green-colored leaves.
5. Under natural season conditions, plants flower on or about November 25 in Southern California.
6. Large inflorescences with salmon pink-colored flower bracts.
7. Good post-production longevity.

In side-by-side comparisons conducted in Encinitas, Calif., plants of the new Poinsettia differ primarily from plants of the mutation parent, 'PER1270', in flower bract color as plants of 'PER1270' have dark red-colored flower bracts.

Plants of the new Poinsettia can be compared to plants of the *Euphorbia pulcherrima* Willd. 'Peterstar Pink', disclosed in U.S. Plant Pat. No. 9,879. In side-by-side comparisons conducted in Encinitas, Calif., plants of the new Poinsettia differed primarily from plants of 'Peterstar Pink' in the following characteristics:

1. Plants of the new Poinsettia had a more upright branching habit than plants of 'Peterstar Pink'.
2. Plants of the new Poinsettia had darker green-colored leaves than plants of 'Peterstar Pink'.
3. Plants of the new Poinsettia and 'Peterstar Pink' differed in flower bract shape as flower bracts of plants of 'Peterstar Pink' were ovate in shape.
4. Plants of the new Poinsettia and 'Peterstar Pink' differed in flower bract color as plants of 'Peterstar Pink' had dark pink-colored flower bracts.

Plants of the new Poinsettia can be compared to plants of the *Euphorbia pulcherrima* Willd. '490 Pink', disclosed in U.S. Plant Pat. No. 8,817. In side-by-side comparisons conducted in Encinitas, Calif., plants of the new Poinsettia differed primarily from plants of '490 Pink' in the following characteristics:

1. Plants of the new Poinsettia and '490 Pink' differed in flower bract shape as flower bracts of plants of '490 Pink' were ovate in shape.
2. Plants of the new Poinsettia and '490 Pink' differed in flower bract color as plants of '490 Pink' had pink-colored flower bracts.
3. Plants of the new Poinsettia flowered about one week later than plants of '490 Pink'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet is a side perspective view of a typical flowering plant of 'PER1912' grown in a container.

The photograph at the top of the sheet is a close-up view of a typical flowering plant of 'PER1912'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 25° C., night temperatures averaged 20° C. and light levels averaged 5,000 foot-candles. Measurements and numerical values represent averages for typical flowering plants. Plants were pinched one time and were 20 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER1912'.

Parentage: Naturally-occurring whole plant mutation of *Euphorbia pulcherrima* Willd. 'PER1270', disclosed in U.S. Plant Pat. No. 24,233.

Propagation:

*Type*.—Terminal vegetative cuttings.

*Time to initiate roots*.—About seven to ten days at night temperatures about 20° C. and day temperatures about 27° C.

*Time to produce a rooted young plant*.—About four weeks at night temperatures about 20° C. and day temperatures about 27° C.

*Root description*.—Fibrous; white in color.

Plant description:

*Plant habit and form*.—Uniform, upright and mounded plant habit; inverted triangle; large inflorescences positioned above the foliar plane; moderately vigorous growth habit.

*Plant height*.—About 37 cm.

*Plant diameter or spread*.—About 54 cm.

*Lateral branch description*.—Quantity: Freely branching habit, about eight lateral branches develop after pinching; upright branching habit. Length: About 32 cm. Diameter: About 7 mm. Internode length: About 2.8 cm. Strength: Strong. Aspect: Initially upright to somewhat outwardly. Texture: Smooth, glabrous. Luster: Glossy. Color: Close to 146A.

*Leaf description*.—Arrangement: Alternate, simple. Length: About 11.5 cm. Width: About 7.4 cm. Shape: Broadly lanceolate with shallow lobes. Apex: Acuminate. Base: Mostly attenuate. Margin: Mostly entire, occasionally with up to four points. Aspect: Flat. Venation pattern: Pinnate, arcuate. Texture, upper surface: Smooth, glabrous; not rugose. Texture, lower surface: Slightly pubescent; prominent venation. Color: Developing and fully expanded leaves, upper surface: Darker green than 139A, venation, close to 147B. Developing and fully expanded leaves, lower surface: Close to N137C; venation, close to midvein, close to 147C. Petioles: Length: About 6 cm. Diameter: About 3 mm. Texture, upper and lower surfaces: Smooth, glabrous. Luster, upper and lower surfaces: Glossy. Color, upper surface: Close to 183B. Color, lower surface: Close to N199C.

Inflorescence description:

*Inflorescence type and habit*.—Terminal inflorescences are compound corymbs of cyathia with colored flower bracts subtending the cyathia; inflorescences uniformly positioned above the foliar plane.

*Fragrance*.—None detected.

*Flowering response*.—Under natural season conditions, plants typically flower on or about November 25 in Southern California; under artificial long nyctoperiod/short photoperiod conditions, plants flower about eight to nine weeks later.

*Post-production longevity*.—Good post-production longevity; plants of the new Poinsettia maintain good substance and flower bract color for about four to six weeks under interior conditions; flower bracts persistent and cyathia not persistent.

*Inflorescence diameter*.—About 32 cm.

*Inflorescence height* (*depth*).—About 8 cm.

*Flower bracts*.—Quantity per inflorescence: About 22. Length, largest bracts: About 15.2 cm. Width, largest bracts: About 10.4 cm. Shape: Mostly elliptical to slightly lanceolate; occasionally with shallow lobes. Apex: Acuminate. Base: Attenuate. Margin: Entire, occasionally with two to three points. Texture, upper and lower surfaces: Smooth, glabrous; satiny; mostly flat, very slightly rugose. Aspect: Upright to horizontal and with development, drooping. Venation pattern: Pinnate, arcuate. Color: Developing or transitional bracts, upper surface: Close to 180C. Developing or transitional bracts, lower surface: Close to 180D. Fully expanded bracts, upper surface: Close to 48A; color does not fade with development. Fully expanded bracts, lower surface: Close to 48B; color does not fade with development. Bract petioles: Length: About 2.5 cm. Diameter: About 2.5 mm. Texture, upper and lower surfaces: Smooth, glabrous. Color, upper and lower surfaces: Close to N34C.

*Cyathia*.—Quantity per corymb: About twelve. Length: About 1.4 cm. Width: About 6 mm. Shape: Oval.

Texture: Smooth, glabrous. Color, inner and outer surfaces: Close to 146A to 146B.

*Nectaries*.—Quantity per cyathium: One, occasionally two. Length: About 6 mm. Width: About 4 mm. Shape: Roughly elliptical to oval. Texture: Smooth, glabrous. Color, inner and outer surfaces: Close to 21A.

*Peduncles*.—Length: About 4 mm. Diameter: About 2 mm. Strength: Strong. Aspect: Mostly upright. Texture: Smooth, glabrous. Color: Close to 146B.

*Reproductive organs*.—Stamens: Quantity per cyathium: About eight. Filament length: About 4 mm. Filament color: Close to 45A. Anther shape: Round; bi-lobed. Anther length: About 1 mm. Anther color: Close to 53A. Amount of pollen: Scarce. Pollen color: Close to 16A. Pistils: Pistil development has not been observed on plants of the new Poinsettia.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER1912' as illustrated and described.

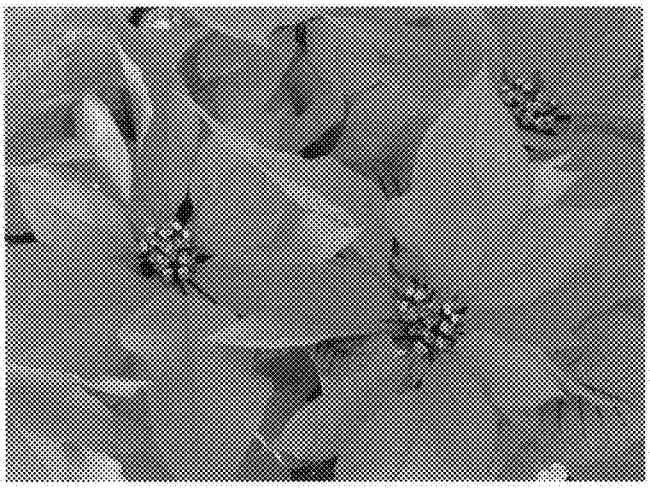
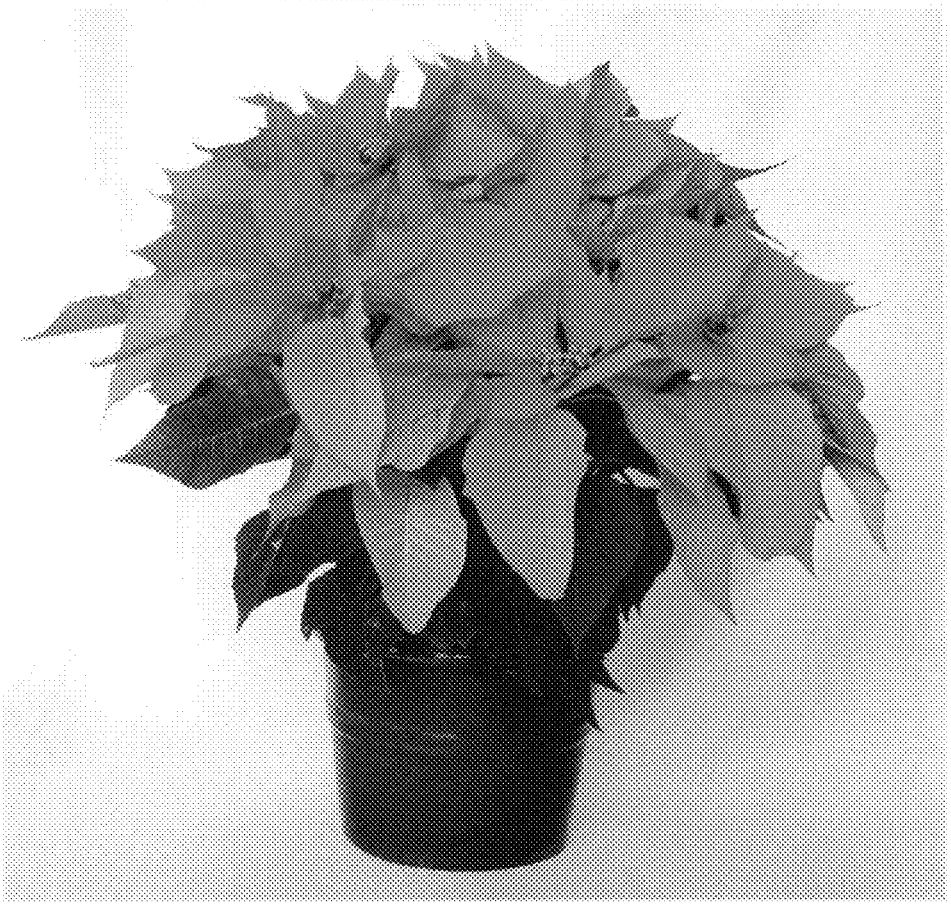

* * * * *